United States Patent [19]

Catrenich et al.

[11] Patent Number: 5,447,923
[45] Date of Patent: Sep. 5, 1995

[54] METHODS AND COMPOSITIONS OF DIPHENYL ETHER PHOSPHATE ESTERS FOR THE TREATMENT OF GASTROINTESTINAL DISORDERS

[75] Inventors: Carl E. Catrenich, Fairfield; Dennis G. A. Nelson, West Chester, both of Ohio

[73] Assignee: The Proctor & Gamble Company, Cincinnati, Ohio

[21] Appl. No.: 321,078

[22] Filed: Oct. 11, 1994

Related U.S. Application Data

[63] Continuation of Ser. No. 124,134, Sep. 20, 1993, abandoned.

[51] Int. Cl.$^6$ .............................................. A61K 31/66
[52] U.S. Cl. ..................................... 514/147; 514/143; 514/144; 514/148
[58] Field of Search ................ 514/147, 143, 144, 148

[56] References Cited

U.S. PATENT DOCUMENTS

| | | | |
|---|---|---|---|
| 3,929,903 | 12/1975 | Noguchi et al. | 260/613 R |
| 4,894,220 | 1/1990 | Nabi et al. | 424/52 |
| 4,980,153 | 12/1990 | Jackson et al. | 434/52 |

FOREIGN PATENT DOCUMENTS

| | | |
|---|---|---|
| 961412 | 1/1975 | Canada . |
| 219912 | 10/1985 | European Pat. Off. . |
| 161899 | 11/1985 | European Pat. Off. . |
| 206625 | 12/1986 | European Pat. Off. . |
| 206626 | 12/1986 | European Pat. Off. . |
| 278744 | 8/1988 | European Pat. Off. . |
| 455475 | 11/1991 | European Pat. Off. . |
| 1022744 | 3/1966 | United Kingdom . |
| 01592011 | 7/1981 | United Kingdom . |
| 93/18741 | 9/1993 | WIPO . |

OTHER PUBLICATIONS

Kamat, N. V., "Biochemical Aspects of Periodontal Diseases: II. The Possible Significance of Calcuium Phosphorus and Alkaline Phosphatase in Human Saliva", *Journal Indian Dent. Asso.*, vol. 50, pp. 171–178 (1978).

Glupczynski, Y. and A. Burette, "Drug Therapy for *Helicobacter pylori* Infection; Problems and Pitfalls" *American J. Gastroenterology*, vol. 85 pp. 1545–1551 (1990).

(List continued on next page.)

*Primary Examiner*—Marianne M. Cintins
*Assistant Examiner*—T. J. Criares
*Attorney, Agent, or Firm*—David L. Suter; Jacobus C. Rasser

[57] ABSTRACT

Methods for the treatment of a human or lower animal subject having an *H. pylori*-mediated upper gastrointestinal disorder comprising administering to said subject a safe and effective amount of a diphenyl ether phosphate ester of the following formula:

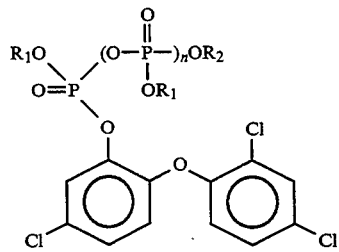

wherein n is an integer from 0 to 3, or a pharmaceutically-acceptable salt thereof.

11 Claims, No Drawings

OTHER PUBLICATIONS

Graham, D. Y. and G. M. A. Börsch, "the Who's and When's of Therapy for *Helicobacter pylori*", *American J. Gastroenterology*, vol. 85, pp. 1552–1555 (1990).

Hiller, S., "A Better Way to Make the Medicine Go Down", *Science*, vol. 253, pp. 1095–1096 (Sept. 6, 1991).

Peterson, W. L., "*Helicobacter pylori* and Peptic Ulcer Disease" 324 New England J. of Medicine 1043 (1991).

Graham, D. Y., G. M. Lew, D. G. Evans, D. J. Evans, Jr., and P. K. Klein, "Effect of Triple Therapy (Antibiotics plus Bismuth) on Duodenal Ulcer Healing", *Annals of Internal Medicine*, vol. 115, pp. 266–269 (1991).

Wyle, F. A., "*Helicobacter pylori:* Current Perspectives", J. Clin. Gastroenterol, (Suppl. 1), S114–S124 (1991).

Blaser, M. J., "*Helicobacter pylori:* Its Role in Disease", *Clinical Infectious Diseases*, pp. 386–391 (1992).

Graham, D. Y., G. M. Lew, P. D. Klein, D. G. Evans, D. J. Evans, Jr., Z. A. Saeed, and H. M. Malaty, "Effect of Treatment of *Helicobacter pylori* infection on the Long–term Recurrence of Gastric or Duodenal Ulcer", *Annals of Internal Medicine*, vol. 116, pp. 705–708 (1992).

Borody, T. J., "Possibilities for *Helicobacter pylori* Suppression/Eradication", European Journal of *Gastroenterology & Hepatology*, vol. 4 (Suppl 2), pp. 537–538 (1992).

Graham, D. Y., "Treatment of Peptic Ulcers Caused by *Helicobacter pylori*" 328 New England J. of Medicine 349 (1993).

Hentschel, E., G. Brandstatter, and B. Dragosics, "Antibiotic Therapy Alone Eradicates *Helicobacter pylori* and Prevents Duodenal Ulcer Recurrence", Gastroenterology, vol. 105, p. 598 (1993).

CA: 233730d, Francis et al, Nov. 29, 1994.

METHODS AND COMPOSITIONS OF DIPHENYL ETHER PHOSPHATE ESTERS FOR THE TREATMENT OF GASTROINTESTINAL DISORDERS This is a continuation of application Ser. No. 08/124,134, filed on Sep. 20, 1993, now abandoned.

BACKGROUND OF THE INVENTION

This invention relates to methods for the treatment of infectious gastrointestinal disorders in humans and other animals.

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these is disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. (The upper gastrointestinal tract as used herein is defined as including the esophagus, the stomach, the duodenum and the jejunum.) Gastritis is, by definition, typified by an inflammation of the stomach mucosa. In practice, though, the disorder is manifested by a broad range of poorly-defined, and heretofore inadequately treated, symptoms such as indigestion, "heart burn", dyspepsia and excessive eructation. A s general discussion of gastfitis appears in B. J. Marshall and J. R. Warren, "Unidentified Curved Bacilli in the Stomach of Patients with Gastritis and Peptic Ulceration", *The Lancet*, (1984), pp. 1311–1315, and in R. Greenlaw, et al., "Gastroduodenitis, A Broader Concept of Peptic Ulcer Disease", Digestive *Diseases and Sciences*, Vol. 25 (1980), pp. 660–672.

Peptic ulcers are lesions of the gastrointestinal tract lining, characterized by loss of tissue due to the action of digestive acids and pepsin. Historically, it was thought that peptic ulcers are caused either by gastric hypersecretion, or (more often) by decreased resistance of the gastric lining to digestive acids and pepsin.

However, since 1982, research has found an association between certain upper gastrointestinal disorders and the presence of a previously unknown organism, *Helicobacter pylori* (originally named "*Campylobacter pylori*" or "*Campylobacter pyloridis.*" (This organism is herein referred to as "*H. pylori.*") See, e.g., Blaser, "*Helicobacter pylori*: Its Role in Disease" 15 *Clinical Infectious Diseases* 386 (1992); Peterson, "*Helicobacter priori* and Peptic Ulcer Disease" 324 *New England J. of Medicine* 1043 (1991); and Wyle, "*Helicobacter pylori*": Current Perspectives 13 J. *Clinical Gastroenterology* S 114 (1991).

The medical literature is replete with methods for treating ulcers, including modification of the diet, surgical removal of the lesions, and the use of drugs. Such drugs include; antacids, which serve to counteract excess gastric secretions; anticholinergics, which reduce acid secretion; H2 antagonists, which also block the release of gastric acids; prostaglandins, which increase the resistance of the gastric lining to digestive fluids, and may also inhibit acid secretion; prokinetic agents, which enhance gastrointestinal tract motility; and compositions which form protective barriers over gastric lesions. Prescription and non-prescription drug therapies are generally described in Garnet, "Antacid Products", *Handbook of Non-prescription Drugs*, 7th edition (1982), Chapter 3.

Regardless of the particular drug composition used in treating gastrointestinal disorders, such as gastritis or peptic ulcer disease, the treatment is often imprecise and incomplete. Actual "cures", i.e., successful treatment resulting in total remission of disease, are very often not effected. See A. J. McLean, et al., "Cyto-protective Agents and Ulcer Relapse", 142 *The Medical Journal of Australia*, Special Supplement S25–28 (1985). Furthermore, many conventional treatments may render subjects hypochlorhydric (i.e., with low levels of hydrochloric acid in the stomach) which may predispose them to other disorders, e.g., gastrointestinal infection, halitosis, and gastric carcinomas.

A variety of treatments have been proposed for *H. priori*-mediated gastrointestinal disorders. These include the use of bismuth salts (such as bismuth subsalicylate and bismuth subcitrate), and antiinfective agents (such as nitroimidazoles, fluoroquinolones, macrolides, nitrofurans, penicillins, and cephalosporins). See, e.g., European Patent Publication 206,625, Marshall, published Dec. 30, 1986; European Patent Publication 206,626 Marshall, published Dec. 30, 1986; European Patent Publication 219,912, Kraft and Morgan, published Oct. 24, 1985, European Patent Publication 282,132, Place, published Sep. 14, 1988; and European Patent Publication 455,475, Dettmar, published May 3, 1990.

However, many of these treatments afford limited success. While killing *H. pylori* is relatively easy in vitro, actual eradication in vivo is very difficult. Currently, single agent antimicrobial approaches designed to eradicate infection by *H. pylori* provide unacceptable eradication rates (i.e., $<80\%$). As a result, multiple antimicrobial agents are commonly used in combination, in particular, a triple-therapy regimen consisting of (1) a bismuth salt (e.g., bismuth subsalicylate), (2) metronidazole and (3) amoxicillin or tetracycline. The reason(s) for single agent failure and triple-therapy success remain ill defined. However, the interrelationship of multiple factors is likely to be important. Of critical significance appears to be the delivery of an appropriate antimicrobial to the gastric niche occupied by *H. pylori* at bactericidal concentrations for an adequate period of time. Delivery is influenced by the formulation, administration and duration of therapy. See, Borody, "Possibilities for *Helicobacter pylori* suppression/eradication" 4 European J. of Gastroenterology & Hepattolog S37 (1992); Glupczynski and Burette, "Drug Therapy for *Helicobacter pylori* Infection: Problems and Pitfalls" 85 American J. Gastroenterology 1545 (1990); Graham and Borsch, "The Who's and When's of Therapy for *Helicobacter pylori*" 85 American J. Gastroenterology 1552 (1990); Hentschel et al., "Antibiotic Therapy Alone Eradicates *Helicobacter pylori* and Prevents Duodenal Ulcer Recurrence" 105 *Gastroenterology* 598 (1993); Graham et al., "Effect of Triple Therapy (Antibiotics plus Bismuth) on Duodenal Ulcer Healing" 115 *Annals of Internal Medicine* 266 (1991); Graham et al., "Effect of Treatment of *Helicobacter pylori* Infection on the Long-term Recurrence of Gastric or Duodenal Ulcer" 116 Annals of Internal Medicine 705 (1992); and Graham, "Treatment of Peptic Ulcers Caused by

*Helicobacter pylori*" 328 New England J. of Medicine 349 (1993).

It has now been discovered that *H. pylori*-mediated upper gastrointestinal disorders can be effectively treated with certain diphenyl ether phosphate esters. In particular, as compared to treatments among those known in the art, these methods are safe and effective to cure, or afford lower relapse rates, of gastritis and peptic ulcer disease mediated by *H. pylori*.

SUMMARY OF THE INVENTION

The present invention provides methods for the treatment of a human or lower animal subject having an upper gastrointestinal disorder comprising administering to said subject a safe and effective amount of a diphenyl ether phosphate ester of the following formula:

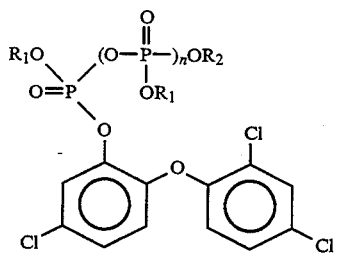

wherein $R_1$ and $R_2$ are hydrogen or a pharmaceutically-acceptable cation; and n is an integer from 0 to 3.

DETAILED DESCRIPTION OF INVENTION

The methods of the present invention comprise treatment of humans or lower animals, having gastrointestinal disorders by administering certain diphenyl ether phosphate esters. In particular, such gastrointestinal disorders are those affecting the upper-gastrointestinal tract, and those mediated by *H. priori* (herein referred to as "*H. priori*"-mediated gastrointestinal disorder(s)." Such gastrointestinal disorders include, for example: *H. priori*-mediated disorders not manifested by presence of ulcerations in the gastric mucosa (herein "non-ulcerative gastrointestinal disorder"), including chronic or atrophic gastritis, non-ulcer dyspepsia, esophogeal reflux disease and gastric motility disorders; and "peptic ulcer disease", i.e., gastric, duodenal and jejunal ulcers.

Diphenyl Ether Phosphate Esters

The methods of this invention comprise administering a compound, or mixtures of compounds, having the following formula:

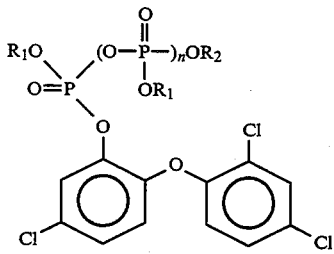

wherein $R_1$ and $R_2$ are hydrogen or a pharmaceutically-acceptable cation; and n is an integer from 0 to 3. Preferred by $R_1$ and $R_2$ are hydrogen or sodium. Preferably, n is 0 or 1; more preferably n is 0.

A "pharmaceutically-acceptable cation" is a cationic salt formed at any acidic (e.g., carboxyl) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium).

A preferred compound of this invention is the monophosphate ester of 2-hydroxy-4,2',4'-trichloro-diphenyl ether (triclosan). The compounds of this invention are made by simple phosphorylation of triclosan, using methods well known in the art. Triclosan, as a starting material, is commercially available. Triclosan disclosed in the following patent documents, incorporated herein by reference: U.S. Pat. No. 3,629,477, Model & Bindlet, issued Dec. 21, 1971; and United Kingdom Pat. No. 01 592 011, Reinhardt & Joachim, published Jul. 1, 1981.

Compositions

Preferred methods of this invention comprise administering a composition comprising:
(a) a safe and effective amount of a diphenyl ether phosphate ester; and
(b) a pharmaceutically-acceptable carrier.

A "safe and effective amount" of a diphenyl ether phosphate ester is an amount that is effective, to inhibit *H. pylori* at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the diphenyl ether phosphate ester therein, and the dosage regimen desired for the composition. As used herein, a "pharmaceutically-acceptable" component is one which is suitable for use with humans and/or animals without undue adverse side effects (such as toxicity, irritation, and allergic response) commensurate with a reasonable benefit/risk ratio.

The compositions of this invention are preferably provided in unit dosage form. As used herein, a "unit dosage form" is a composition of this invention containing an amount of a diphenyl ether phosphate ester that is suitable for administration to a human or lower animal subject., in a single dose, according to good medical practice. These compositions preferably contain from about 50 mg (milligrams) to about 2,000 mg, more preferably from about 100 mg to about 1,500 mg, more preferably from about 500 mg to about 1,000 mg, of a diphenyl ether phosphate ester.

The compositions of this invention may be in any of a variety of forms, suitable (for example) for oral administration. Preferred compositions of this invention comprise:
(a) a safe and effective amount of a diphenyl ether phosphate ester; and
(b) a pharmaceutically-acceptable gastric delivery carrier.

As used herein, a "gastric delivery carrier" is a delivery means for the diphenyl ether phosphate ester which is suitable for oral ingestion and which delivers the ester to the upper or lower gastrointestinal tract. Preferably, the gastric delivery carrier delivers said ester to the stomach.

A variety of pharmaceutically-acceptable gastric delivery carriers well-known in the art may be used. These include solid or liquid fillers, diluents, hydrotropes, surface-active agents, and encapsulating substances. The amount of carder employed in conjunction with the diphenyl ether phosphate ester is sufficient to provide a practical quantity of material for administration per unit dose. Techniques and compositions for making dosage forms useful in the methods of this invention are described in the following references, all incorporated by reference herein: 7 *Modem Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the diphenyl ether phosphate ester. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

Preferably the compositions of this invention have a pH of from about 4.0 to about 8,5, preferably from about 4.0 to about 7.4. The pH of the compositions may be modified using pharmaceutically-acceptable buffers, including (for example) acetate, bicarbonate, and phosphate buffers.

Methods of Administration

This invention provides methods of treating or preventing an *H. priori*-mediated gastrointestinal disorder in a human or other animal subject, by administering a safe and effective amount of a diphenyl ether phosphate ester to said subject.

As used herein, "administering" refers to any method which, in sound medical practice, delivers the compounds or compositions used in this invention to the subject to be treated in such a manner so as to be effective in the treatment of the gastrointestinal disorder. Preferably, the diphenyl ether phosphate ester is administered orally. As used herein, "administering" refers to any method which, in sound medical practice, delivers the compounds or compositions used in this invention to the subject to be treated in such a manner so as to be effective in the treatment of the gastrointestinal disorder. Preferably, the diphenyl ether phosphate ester is administered orally. The specific dosage of diphenyl ether phosphate ester to be administered, as well as the duration of treatment, are mutually dependent. The dosage and treatment regimen will also depend upon such factors as the diphenyl ether phosphate ester used, the ability of the diphenyl ether phosphate ester to reach minimum inhibitory concentrations at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 50 mg to about 5,000 mg, more preferably from about 100 mg to about 2,000 mg, more preferably from about 200 mg to about 1,000 mg, of diphenyl ether phosphate ester are administered per day. Treatment regimens preferably extend from about 7 to about 56 days, preferably from about 7 to about 28 days, more preferably from about 7 to about 21 days, in duration.

Optional Actives

Optional pharmaceutically-active materials may be used in the methods of this invention, and included in the compositions of this invention, which do not substantially interfere with the antimicrobial activity of the diphenyl ether phosphate ester. Preferred optional active materials are those which suppress lower stomach acidity (herein as "acid suppression agent"). Among such preferred acid suppression agents are metallic antacid salts. Such salts include, for example, aluminum carbonate, aluminum hydroxide, aluminum phosphate, aluminum hydroxycarbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilcate, and mixtures thereof. Particularly preferred antacid salts include calcium carbonate, magnesium carbonate, and aluminum magnesium hydroxide sulfate.

Other preferred optional actives include $H_2$ blocking anti-secretory agents. $H_2$ blocking agents among those useful herein include (for example) cimetidine, ranitidine, famotidine, nizatidine, burimamide, metiamide, tiotidine, oxmetidine, and mixtures thereof. Preferred $H_2$ blocking agents include cimetidine, ranitidine, nizatidine, and famotidine.

Other preferred acid suppression agents are the protar pump inhibitors. Such inhibitors include (for example) omeprazole, lansoprazole, pantoprazole, and mixtures thereof.

Other preferred optional actives include bismuth salts. Such salts include, for example, bismuth aluminate, bismuth citrate, bismuth nitrate, bismuth subcarbonate, bismuth subgalate, bismuth subsalicylate, and mixtures thereof. A particularly preferred bismuth salt is bismuth subsalicylate.

The methods of this invention may also comprise administering an antimicrobial. Antimicrobials among those useful herein include (for example) the aminoglycosides, such as gentamicin, neomycin, kanamycin and streptomycin; the macrolides, such as erythromycin, clindamycin, rifampin, and azithromycin; the penicillins, such as penicillin G, penicillin V, ampicillin and amoxycillin; the polypeptides, such as bacitracin and polymyxin; the tetracyclines, such as tetracycline, chlortetracyclin, oxytetracycline, and doxycycline; the cephalosporins, such as cephalexin and cephalothin; the quinolones, such as ciprofloxacin, and ofloxacin; the nitrofurans, such as furazolidone and nitrofurantoin; the sulfonamides; metranidazole; tinidazole; nimorazole; and mixtures thereof. Preferred antimicrobials include metronidazole, amoxycillin, tetracycline, and mixtures thereof.

The following non-limiting examples illustrate the methods of the present invention.

EXAMPLE 1

A diphenyl ether phosphate ester, triclosan monophosphonate, is made by the following general procedure. A 3-liter, 3-neck round-bottom flask equipped with a mechanical stirrer and an addition funnel is charged with triclosan (200 g), (Irgacare MP, HX533, from Ciba-Geigy). Phosphoryl chloride (128 ml) is added and mechanical stirring is begun. After the triclosan is dissolved, the vessel is immersed in an ice-water bath and the solution is stirred for a further 10 minutes. Triethylamine (106 ml) is introduced dropwise via the addition funnel over the course of about 30 minutes. The resulting viscous mixture is stirred for an additional 90 minutes at 0° C., and then for 30 minutes at room temperature.

Diethyl ether (500 ml) is introduced to the reaction flask with stirring, transforming the viscous reaction mixture to a granular suspension. The vessel is again cooled to 0° C. and water (500 ml) is added very slowly, dropwise, over 30 minutes. The dropping rate for the first 100 ml is 1 drop every 2 seconds. The resulting amber, biphasic system which results upon completion of the hydrolysis is stirred at 0° C. for an additional 2 hours, then at ambient temperature overnight.

Diethyl ether (500 ml) is added to the mixture with stirring. The entire contents of the flask is transferred to a separatory funnel. The lower, aqueous phase is drained off and extracted twice with 500 ml portions of diethyl ether. The original ether phase from the reaction mixture is combined with these two subsequent ether extracts. The acidic aqueous phase is discarded.

The ether solution, containing primarily triclosan monophosphate and a phosphodiester by-product, is extracted with 4×1 liter portions of 1N NaOH. The combined NaOH extracts are back extracted with 2×500 ml diethyl ether. These ether extracts are added to the original ether solution. At this stage, the NaOH solution (pH 12–14) contains pure triclosan monophosphate, while the ether solution contains primarily a phosphodiester by-product, along with traces of unreacted triclosan.

The NaOH solution is acidified with concentrated HCl to pH 1.0±0.2, and is extracted with 3×1 liters of diethyl ether. The combined extracts are dried (MgSO4), filtered, and concentrated in vacuo to an oil. The oil is triturated with dichloromethane (3 liters) which induces crystallization. The resulting white solid is filtered using a BPGchner funnel, then dried in vacuo at 25° C. for 24–48 hours. This material if not pure enough at this stage can further be purified by again dissolving in 1N NaOH as previously described, then extracted with diethyl ether, removal of the ether layer and adjustment of the resulting water layer with HCl to pH=1 followed by extraction with ether. Then the resulting ether layer is dried with Mg SO4 and the volatiles removed by roto-evaporation and then vacuum dried at 25° C. for 24–72 hours.

A human subject, suffering from atrophic gastritis, is treated by a method of the present invention. Specifically, the subject is endoscoped and a biopsy taken of the gastric mucosa of the subject. Analysis of the biopsy sample shows inflammation of the mucosa, and depletion of the protective mucous layer. Histological examination of the sample also reveals the presence of *H. pylori*. The subject is then treated, according to the present invention, by administering a composition comprised as follows:

| Component | Amount | Wt. % |
| --- | --- | --- |
| Triclosan monophosphate | 500.0 mg | 8.58 |
| Veegum (MgAlSilicate-suspending agent) | 60.5 mg | 1.04 |
| Methocel 4000 (HPMC-thickening agent) | 82.5 mg | 1.42 |
| saccharin sodium (sweetener) | 49.5 mg | 0.09 |
| glycerol (humectant, sweetener) | 137.5 mg | 2.36 |
| flavor | 1.8 mg | 0.03 |
| water | 5000.0 mg | 85.8 |
| TOTAL | 5.832 g | 100.00 |

The compositions administered 3 times daily in equal doses of 500 milligrams (for a total of 1,500 milligrams of diphenyl ether phosphate ester administered per day) for 14 days. Thereafter, the subject is endoscoped and biopsied again, finding essentially normal, healed gastric mucosa. Histological examination of the gastric material sample does not reveal any bacterial infection. The subject remains asymptomatic, and another biopsy performed five months later reveals normal gastric mucosa.

EXAMPLE 2

A capsule composition according to this invention is made as follows.

| Component | Amount | Wt. % |
| --- | --- | --- |
| Triclosan monophosphate | 250.0 mg | 33.33 |
| Pluronic F-108 (non-ionic surfactant) | 250.0 mg | 33.33 |
| PEG 1450 (solubilizer) | 250.0 mg | 33.33 |
| TOTAL | 750.0 mg | 100.00 |

A human subject, suffering from peptic ulcer disease, is treated by a method of the present invention. Specifically, a biopsy of gastric mucosa is taken from the stomach of the subject. Histological examination of the mucosa reveals the presence of *H. pylori*.

The subject is then treated by orally administering one of the capsules three times daily (for a total of 750 milligrams of diphenyl ether phosphate ester administered per day), for 21 days. Concurrently, the subject is administered omeprazole in a single 20 milligram dose, daily, for 21 days. Thereafter, the subject is endoscoped, revealing normal gastric mucosa and healing of the peptic ulcer crater. In the above example, other acid suppression agents, including metallic antacid salts and $H_2$ blocking antisecretory agents, are substituted for omeprazole with substantially similar results.

What is claimed is:

1. A method for the treatment of a human or lower animal subject having an *H. pylori*-mediated gastrointestinal disorder, comprising administering to said subject a safe and effective amount of a diphenyl ether phosphate ester of the formula:

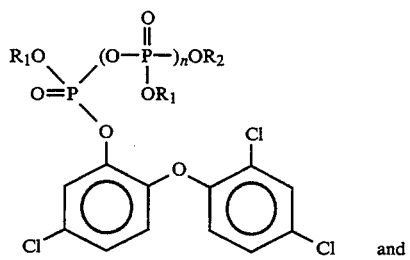

wherein $R_1$ and $R_2$ are hydrogen or a pharmaceutically-acceptable cation; and n is an integer from 0 to 3.

2. A method according to claim 1, wherein n is 0.

3. A method according to claim 2, wherein said diphenyl ether phosphate ester is administered to said subject at a level of from about 100 to about 2,000 milligrams per day, for from 7 to 28 days.

4. A method according to claim 1, additionally comprising administering an acid suppression agent.

5. A method according to claim 4, wherein said acid suppression agent is a metallic antacid salt.

6. A method according to claim 4, wherein said acid suppression agent is an $H_2$ blocking antisecretory agent.

7. A method according to claim 4, wherein said acid suppression agent is a protar pump inhibitor.

8. A method according to claim 1, additionally comprising administering a bismuth salt.

9. A composition for the treatment of an *H. pylori*-mediated gastrointestinal disorder, comprising:
(a) a safe and effective amount of a diphenyl ether phosphate ester having the formula

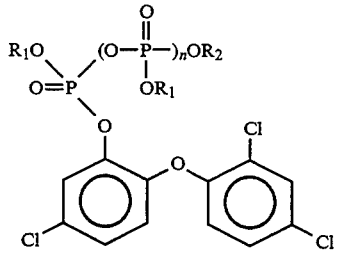

wherein $R_1$ and $R_2$ are hydrogen or a pharmaceutically-acceptable cation, and n is an integer from 0 to 3;
(b) an acid suppression agent; and
(c) a pharmaceutically-acceptable gastric delivery carrier.

10. A composition according to claim 9, wherein said composition has a pH of from about 4.0 to about 7.4.

11. A composition according to claim 9, wherein said acid suppression agent is a metallic antacid salt.

* * * * *